(12) United States Patent
Benzel et al.

(10) Patent No.: US 6,214,005 B1
(45) Date of Patent: *Apr. 10, 2001

(54) SPINAL COLUMN RETAINING APPARATUS

(75) Inventors: Edward C. Benzel, Albuquerque, NM (US); Hansen A. Yuan, Fayetteville, NY (US); Alex Dinello, Palo Alto, CA (US); Michael H. Wefers, South Euclid, OH (US); Aaron C. Smith, Gibsonia, PA (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/141,920

(22) Filed: Aug. 28, 1998

Related U.S. Application Data

(63) Continuation of application No. 09/655,851, filed on Aug. 31, 1996, now Pat. No. 5,800,433.

(51) Int. Cl.⁷ .................................................. A61B 17/70
(52) U.S. Cl. ........................................... 606/61; 623/17.11
(58) Field of Search ...................... 606/60, 61; 623/17.11

(56) References Cited

U.S. PATENT DOCUMENTS

| | | |
|---|---|---|
| 4,041,939 | 8/1977 | Hall . |
| 4,047,524 * | 9/1977 | Hall ......................................... 606/61 |
| 4,289,123 * | 9/1981 | Dunn ....................................... 606/61 |
| 4,484,570 | 11/1984 | Sutter et al. . |
| 5,024,213 | 6/1991 | Asher et al. . |
| 5,041,113 * | 8/1991 | Biedermann et al. .................. 606/61 |
| 5,092,893 * | 3/1992 | Smith ....................................... 623/17 |
| 5,147,360 | 9/1992 | Dubousset . |
| 5,152,303 | 10/1992 | Allen . |
| 5,180,381 * | 1/1993 | Aust et al. ............................... 606/61 |
| 5,261,911 | 11/1993 | Carl . |
| 5,380,324 | 1/1995 | Müller et al. . |
| 5,395,372 * | 3/1995 | Holt et al. ............................... 606/61 |
| 5,403,314 | 4/1995 | Currier . |
| 5,454,812 * | 10/1995 | Lin .......................................... 606/61 |
| 5,498,263 | 3/1996 | DiNello et al. . |
| 5,522,816 | 6/1996 | DiNello et al. . |
| 5,662,652 | 9/1997 | Schäfer et al. . |
| 5,667,506 * | 9/1997 | Sutterlin ................................. 606/61 |
| 5,681,312 * | 10/1997 | Yuan et al. .............................. 606/61 |
| 5,683,391 * | 11/1997 | Boyd ....................................... 606/61 |
| 5,683,392 * | 11/1997 | Richelsoph et al. ................... 606/61 |
| 5,713,900 * | 2/1998 | Benzel et al. .......................... 606/61 |
| 5,800,433 | 9/1998 | Benzel et al. .......................... 606/61 |

FOREIGN PATENT DOCUMENTS

| | | |
|---|---|---|
| 0 570 929 | 11/1993 | (EP) . |
| 0 599 640 | 6/1994 | (EP) . |
| 0 679 370 | 11/1995 | (EP) . |
| 2 713 473 | 6/1995 | (FR) . |

* cited by examiner

*Primary Examiner*—Gene Mancene
*Assistant Examiner*—Michael B. Priddy

(57) ABSTRACT

An apparatus for retaining first and second vertebrae of a spinal column in a desired spatial relationship includes a longitudinal member positionable along the spinal column. A member, such as a plate, connectable with the first vertebra has first and second fastener openings and a portion engageable with the longitudinal member. A first fastener extendable through the first fastener opening in the member has a first end portion for attachment to the first vertebra and has a longitudinal axis. A second fastener extendable through the second fastener opening in the member has a first end portion for attachment to the first vertebra and has a longitudinal axis. The longitudinal axes of the first and second fasteners converge at an acute angle as viewed in a sagittal plane when the first and second fasteners connect the member with the first vertebra. The member connectable with the first vertebra has a body portion and has a lip portion projecting from the body portion of the member. The lip portion of the member is engageable with a surface of the first vertebra facing toward the second vertebra.

23 Claims, 7 Drawing Sheets

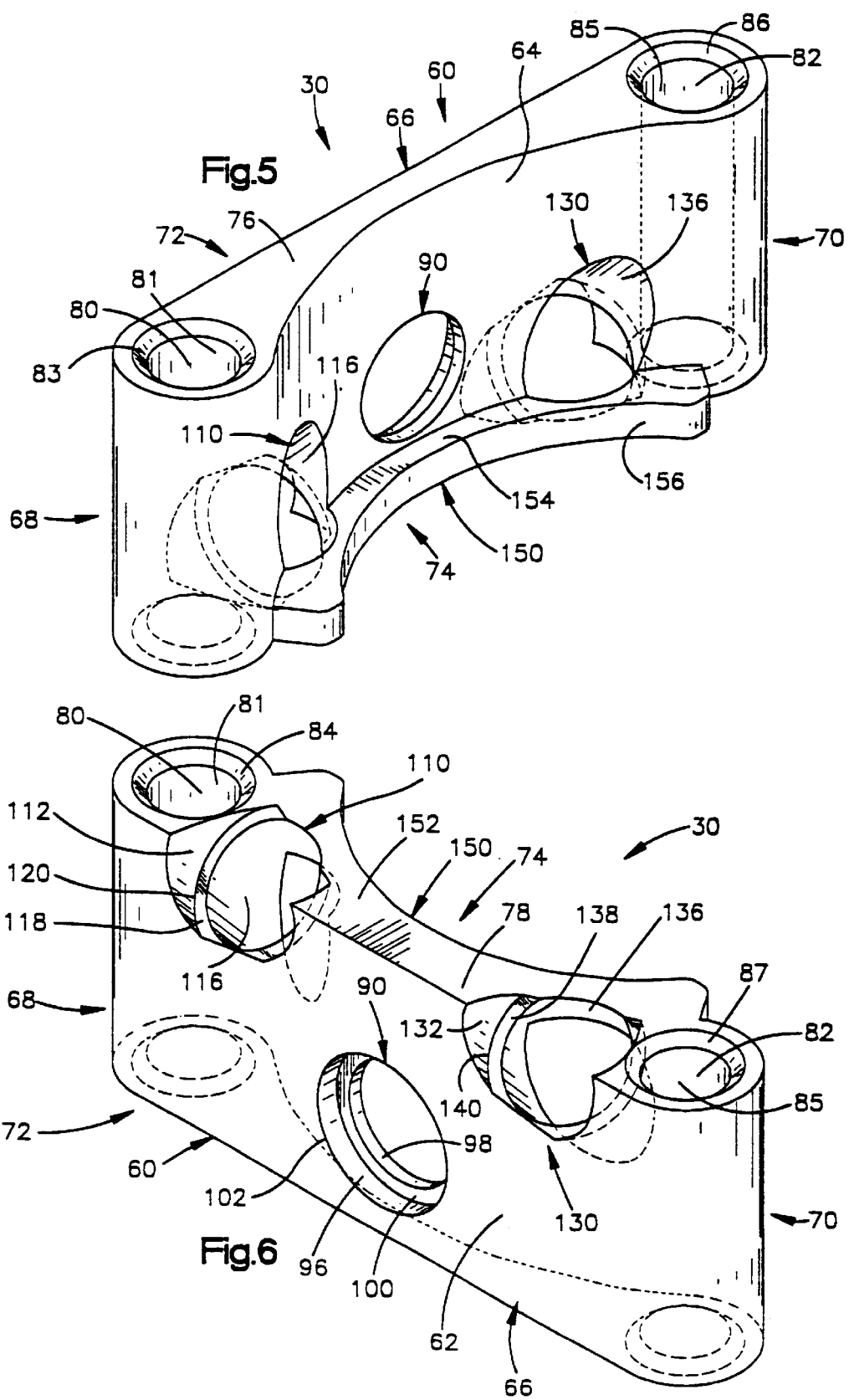

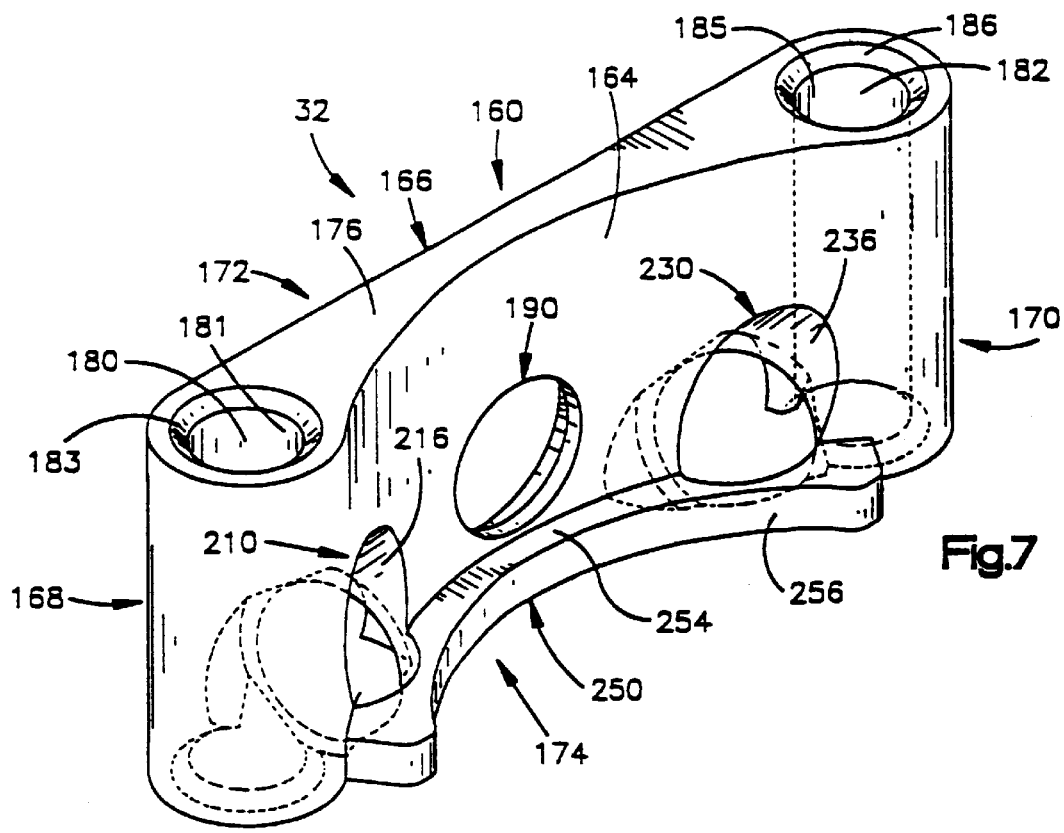
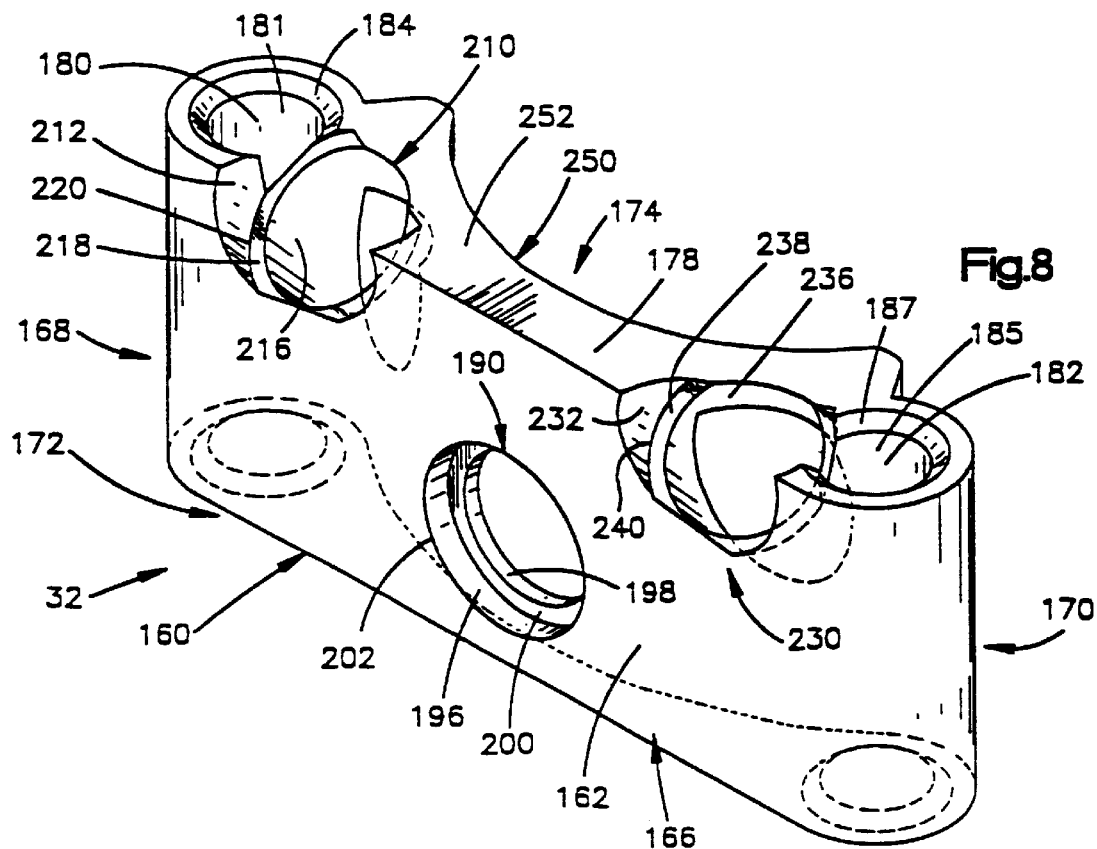

SPINAL COLUMN RETAINING APPARATUS

This application is a continuation of co-pending application Ser. No. 09/655,851, filed on Aug. 31, 1996, now U.S. Pat. No. 5,800,433.

BACKGROUND OF THE INVENTION

1. Technical Field

The present invention relates to an apparatus for use in retaining vertebrae of a spinal column in a desired spatial relationship. In particular, the present invention relates to an apparatus for use in retaining cervical vertebrae of a human spinal column in a desired spatial relationship.

2. Description of the Prior Art

There are various known devices for retaining vertebrae of a spinal column in a desired spatial relationship. Certain of such known devices include rods connected to and extending between vertebrae and certain of such known devices include plates connected to and extending between vertebrae.

SUMMARY OF THE INVENTION

The present invention is an apparatus for retaining first and second vertebrae of a spinal column in a desired spatial relationship. The apparatus includes a longitudinal member positionable along the spinal column. A member connectable with the first vertebra has first and second fastener openings and a portion engageable with the longitudinal member. A first fastener is extendable through the first fastener opening in the member to connect the member with the first vertebra. The first fastener has a first end portion for attachment to the first vertebra and has a longitudinal axis. A second fastener is extendable through the second fastener opening in the member to connect the member with the first vertebra. The second fastener has a first end portion for attachment to the first vertebra and has a longitudinal axis.

In accordance with one feature of the present invention, the longitudinal axis of the first fastener and the longitudinal axis of the second fastener converge at an acute angle as viewed in the sagittal plane when the first and second fasteners connect the member with the first vertebra. The apparatus also includes means for connecting the longitudinal member with the second vertebra.

In accordance with another feature of the present invention, the member connectable with the first vertebra has a body portion. The member also has a lip portion projecting in a first direction from the body portion of the member. The lip portion of the member is engageable with a surface of the first vertebra facing toward the second vertebra.

BRIEF DESCRIPTION OF THE DRAWINGS

The foregoing and other features of the present invention will become more apparent to one skilled in the art upon reading the following description with reference to the accompanying drawings, wherein:

FIG. 5 is a perspective view of a first plate which forms a portion of the apparatus of FIG. 1;

FIG. 6 is another perspective view of the plate of FIG. 5;

FIG. 7 is a view similar to FIG. 5 of a second plate which forms a portion of the apparatus of FIG. 1;

FIG. 8 is another perspective view of the plate of FIG. 7;

DESCRIPTION OF PREFERRED EMBODIMENTS

Figure 1:
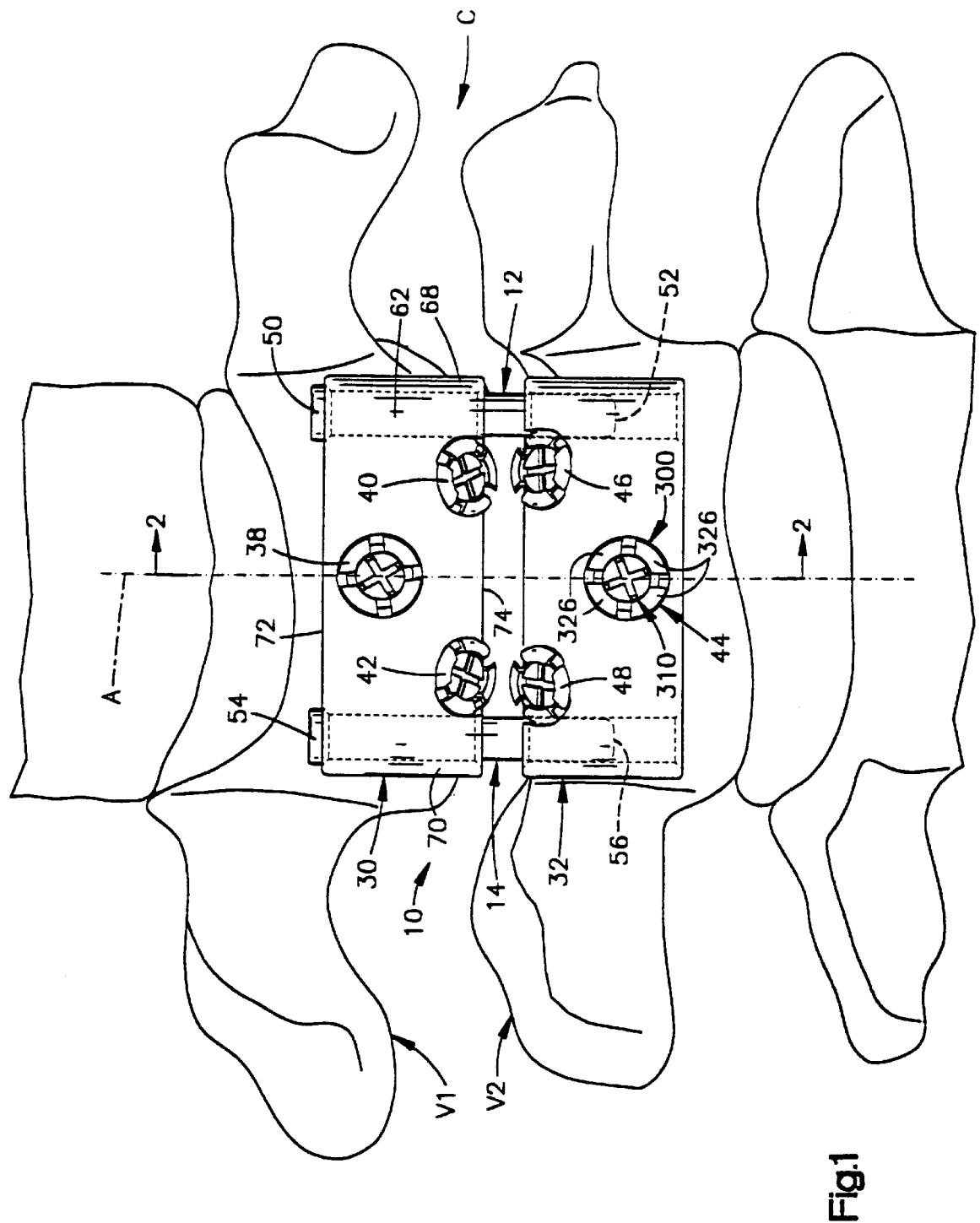
FIG. 1 is an elevational view of an apparatus constructed in accordance with the present invention for maintaining a desired spatial relationship between cervical vertebrae of a spinal column.

The present invention relates to an apparatus for use in retaining vertebrae of a spinal column in a desired spatial relationship. As representative of the present invention, FIG. 1 illustrates an apparatus 10 for use in retaining bone portions such as cervical vertebrae V1 and V2 of a human spinal column C in a desired spatial relationship. The spinal column C has an axis A which is a vertical axis of the human body.

Figure 2:
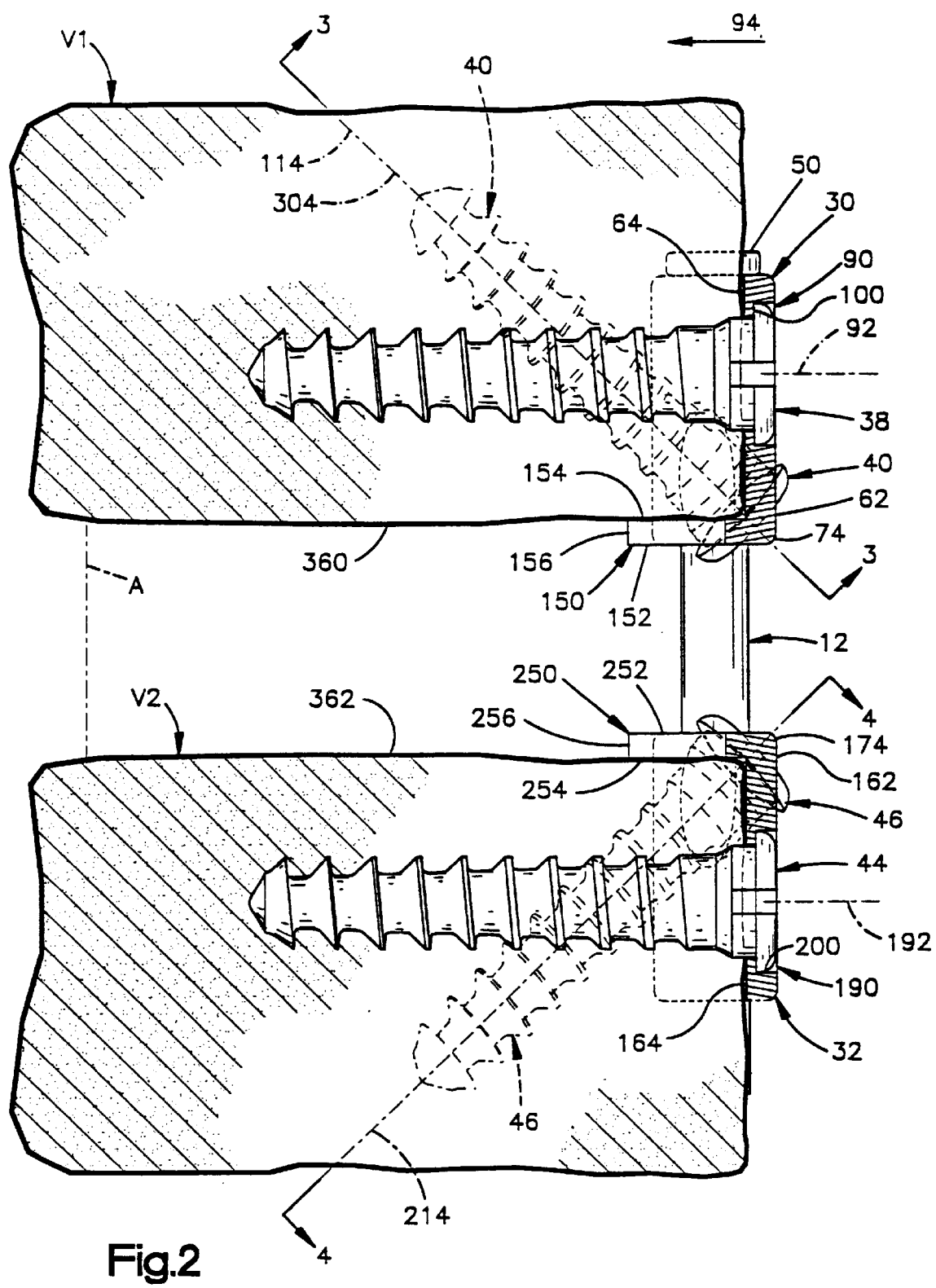
FIG. 2 is a view of the apparatus of FIG. 1, taken along the sagittal plane as indicated by line 2—2 of FIG. 1.

The apparatus 10 includes a pair of surgically implantable rods 12 and 14 (FIGS. 1 and 2). The apparatus 10 also includes first and second members or plates 30 and 32 which engage the rods 12 and 14; three fasteners 38, 40, and 42 for connecting the first plate with the first vertebra V1; and three fasteners 44, 46, and 48 for connecting the second plate with the second vertebra V2.

The first rod 12 (FIG. 1) is made of a suitable biocompatible material, such as titanium or stainless steel. The first rod 12 has an elongate cylindrical configuration and has a circular cross section taken in a plane extending perpendicular to the longitudinal central axis of the first rod. The first rod 12 has a smooth outer surface. A first end portion of the first rod 12 is formed as a cap 50. The first rod 12 also has a second end portion 52 opposite from the first end portion 50.

The second rod 14 is identical to the first rod 12. The second rod 14 has a first end portion which is formed as a cap 54. The second rod 14 also has a second end portion 56 opposite from the first end portion 54. The rods 12 and 14 are bendable to a desired configuration to conform to a desired curvature of the spinal column C. The rods 12 and 14 together have sufficient strength and rigidity to maintain the vertebrae V1 and V2 in a desired spatial relationship.

The rods 12 and 14 have a length which is sufficient to enable the rods to span at least the two vertebrae V1 and V2. The length of the rods 12 and 14 will depend upon the condition to be corrected and the number of vertebrae to be held in a desired spatial relationship relative to each other by the apparatus 10. If more than two vertebrae are to be held in a desired spatial relationship relative to each other by the apparatus 10, the rods 12 and 14 would be longer and more than two plates, such as the plates 30 and 32, may be used.

The first plate 30 (FIGS. 5 and 6) is made of a suitable biocompatible material, such as titanium or stainless steel. The first plate 30 includes a main body portion 60. The main body portion 60 of the first plate 30 has a planar outer side surface 62 for facing anteriorly or away from the first vertebra V1. The first plate 30 has an arcuate inner side surface 64 for facing posteriorly or toward the first vertebra V1. The inner side surface 64 of the first plate 30 may engage the anterior surface of the first vertebra V1 when the first plate is connected with the first vertebra as described below.

Figure 3:
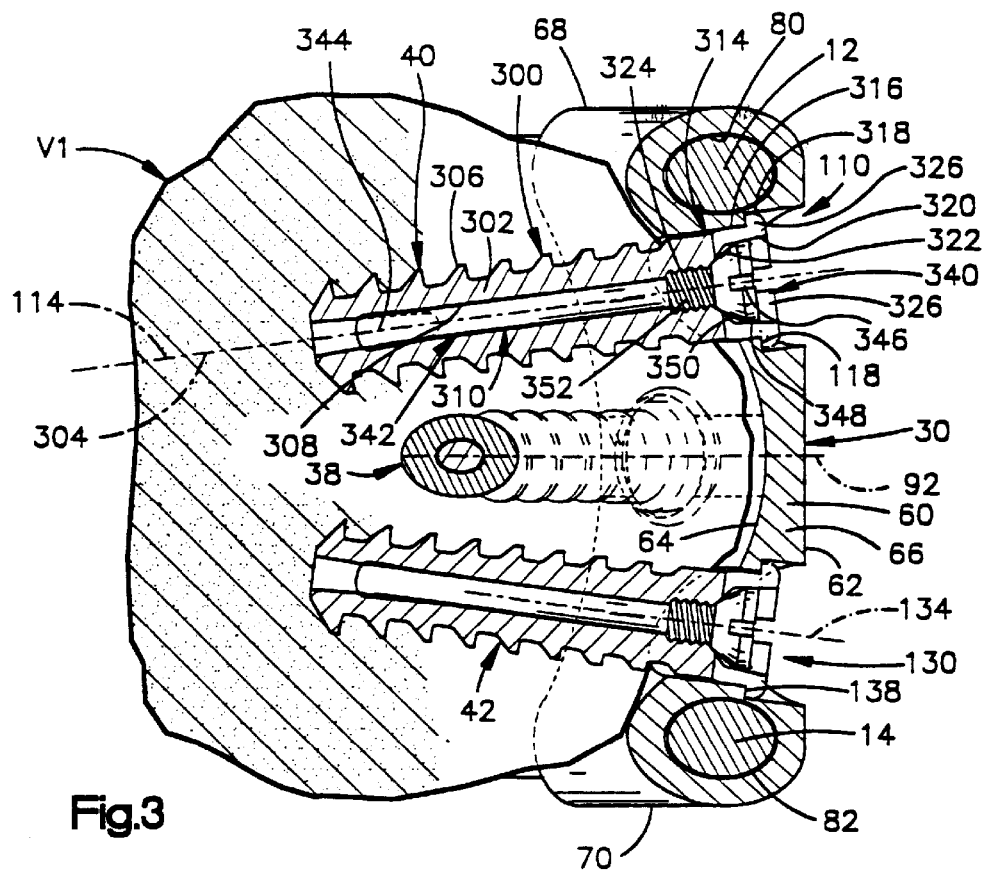
FIG. 3 is a sectional view taken generally along line 3—3 of FIG. 2.

The main body portion 60 of the first plate 30 has a central portion 66 which extends laterally between a first side portion 68 and a second side portion 70 of the first plate. Because the inner side surface 64 of the first plate 30 has an arcuate configuration, the central portion 66 of the first plate is relatively thin (as viewed in a direction from left to right in FIG. 3) as compared to the first side portion 68 and to the second side portion 70.

The main body portion 60 of the first plate 30 also has first and second end portions 72 and 74. The first end portion 72 of the first plate 30 includes a planar first end surface 76 of the first plate 30. The second end portion 74 includes a planar second end surface 78 of the first plate 30. The second end surface 78 extends parallel to the first end surface 76.

A first rod passage 80 is formed in the first side portion 68 of the first plate 30. The first rod passage 80 is an opening which extends between the first and second end surfaces 76 and 78 of the first plate 30 in a direction parallel to the planar outer side surface 62 of the first plate. The first rod passage 80 is defined by a cylindrical surface 81 and tapered pilot surfaces 83 and 84 at opposite ends of the cylindrical surface 81. The diameter of the cylindrical surface 81 is slightly greater than the diameter of the first rod 12, so that the first rod and the first plate 30 can be relatively movable.

The second side portion 70 of the first plate 30 is a mirror image of the first side portion 68. A second rod passage 82 is formed in the second side portion 70 of the first plate 30. The second rod passage 82 is an opening which extends between the first and second end surfaces 76 and 78 of the first plate 30 in a direction parallel to the planar outer side surface 62 of the first plate. The second rod passage 82 extends parallel to the first rod passage 80. The second rod passage 82 is defined by a cylindrical surface 85 and tapered pilot surfaces 86 and 87 at opposite ends of the cylindrical surface 85. The diameter of the second rod passage 82 is the same as the diameter of the first rod passage 80. The diameter of the cylindrical surface 85 is slightly greater than the diameter of the second rod 14, so that the second rod and the first plate 30 can be relatively movable.

A circular first fastener opening 90 extends through the central portion 66 of the first plate 30. The first fastener opening 90 has an axis 92 (FIG. 2) which extends perpendicular to the plane of the outer side surface 62 of the first plate 30. The axis 92 extends in a first direction as indicated by the arrow 94, that is, from right to left as viewed in FIG. 2, when the first plate 30 is mounted on the first vertebra V1. The first direction 94 extends perpendicular to the axes of the rods 12 and 14.

The first fastener opening 90 is partially defined by a larger diameter cylindrical surface 96 (FIG. 6) which extends from the outer side surface 62 of the first plate 30 in a direction into the material of the central portion 66 of the first plate. The cylindrical surface 96 is centered on the axis 92 of the first fastener opening 90. The first fastener opening 90 is partially defined by a smaller diameter cylindrical surface 98 which extends from the inner side surface 64 of the first plate 30 in a direction into the material of the central portion 66 of the first plate to a location spaced radially inward from the surface 96. The cylindrical surface 98 is centered on the axis 92 of the first fastener opening 90.

An annular shoulder surface 100 (FIGS. 2 and 6) extends radially (relative to the axis 92) between the cylindrical surfaces 96 and 98. The shoulder surface 100 and the larger diameter cylindrical surface 96 define a recess 102 in the outer side surface 62 of the first plate 30.

The main body portion 60 of the first plate 30 also includes a circular second fastener opening 110 formed at a location adjacent to, but spaced apart from, the first rod passage 80 in the first side portion 68 of the first plate. The second fastener opening 110 extends through both the second end surface 78 of the first plate 30 and the outer side surface 62 of the first plate.

The second fastener opening 110 is partially defined by a larger diameter cylindrical surface 112 (FIG. 6) which extends from the outer side surface of the first plate 30 in a direction into the material of the first side portion 68 of the first plate. The cylindrical surface 112 is centered on an axis 114 (FIG. 2) of the second fastener opening 110. The cylindrical surface 112 is spaced apart from the first rod passage 80.

The second fastener opening 110 is partially defined by a smaller diameter cylindrical surface 116 (FIG. 6) which extends from the inner side surface 64 of the first plate 30 in a direction into the material of the first side portion 68 of the first plate, to a location spaced radially inward from the surface 112. The cylindrical surface 116 is centered on the axis 114 of the second fastener opening 110.

An annular shoulder surface 118 (FIGS. 3 and 6) extends radially (relative to the axis 114) between the cylindrical surfaces 112 and 116. The shoulder surface 118 and the larger diameter cylindrical surface 112 define a recess 120 in the outer side surface 62 of the first plate 30.

The axis 114 of the second fastener opening 110 extends transverse to the axis 92 of the first fastener opening 90. Specifically, the axis 114 (FIG. 3) of the second fastener opening 110 converges with the axis 92 of the first fastener opening 90 as viewed in a transverse plane at right angles to the vertical axis A, as can be seen from FIG. 3. In the illustrated embodiment, the axis 114 converges at an angle of about 100 with the axis 92 as viewed in this transverse plane.

The axis 114 of the second fastener opening 110 also converges with the axis 92 of the first fastener opening 90 as viewed in the sagittal plane, as can be seen in FIG. 2. In the illustrated embodiment, the axis 114 converges at an angle of 45° with the axis 92 as viewed in the sagittal plane. It is contemplated that the angle of convergence as viewed in the sagittal plane could be in the range of from about 30° to about 60°.

The main body portion 60 of the first plate 30 also includes a circular third fastener opening 130 formed at a location adjacent to, but spaced apart from, the second rod passage 82 in the second side portion 70 of the first plate. The third fastener opening 130 extends through both the second end surface 78 of the first plate 30 and the outer side surface 62 of the first plate.

Figure 4:
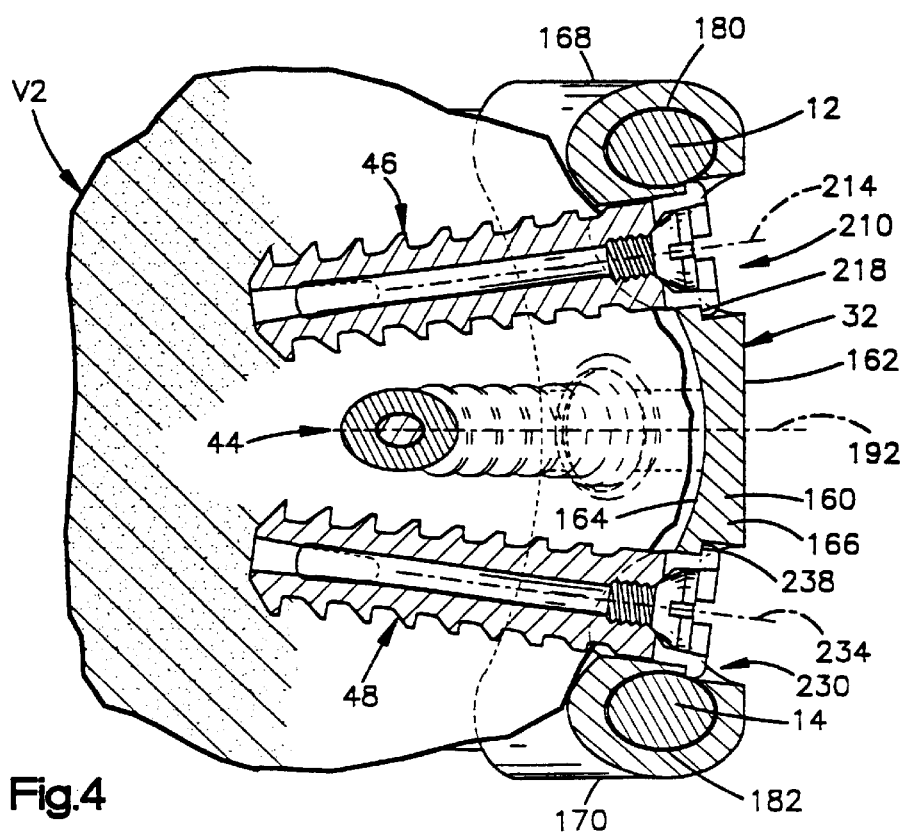
FIG. 4 is a sectional view taken generally along line 4—4 of FIG. 2.

The third fastener opening 130 is partially defined by a larger diameter cylindrical surface 132 (FIG. 6) which extends from the outer side surface 62 of the first plate 30 in a direction into the material of the second side portion 70 of the first plate. The cylindrical surface 132 is centered on an axis 134 (FIG. 4) of the third fastener opening 130. The cylindrical surface 132 is spaced apart from the second rod passage 82.

The third fastener opening 130 is partially defined by a smaller diameter cylindrical surface 136 (FIG. 6) which extends from the inner side surface 64 of the first plate 30 in a direction into the material of the second side portion 70 of the first plate, to a location spaced radially inward from the surface 32. The cylindrical surface 136 is centered on the axis 134 of the third fastener opening 130.

An annular shoulder surface 138 (FIGS. 3 and 6) extends radially (relative to the axis 134) between the cylindrical surfaces 132 and 136. The shoulder surface 138 and the larger diameter cylindrical surface 132 define a recess 140 in the outer side surface 62 of the first plate 30.

The axis 134 (FIG. 3) of the third fastener opening 130 is coplanar with the axis 114 of the second fastener opening 110. The axis 134 of the third fastener opening 130 extends transverse to the axis 92 of the first fastener opening 90. Specifically, the axis 134 of the third fastener opening 130 converges with the axis 92 of the first fastener opening 90 as viewed in a transverse plane at right angles to the vertical axis A, as can be seen from FIG. 3. In the illustrated embodiment, the axis 134 converges with the axis 92 at an angle of 10° as viewed in this transverse plane.

The axis 134 of the third fastener opening 130 also converges with the axis 92 of the first fastener opening 90 as viewed in the sagittal plane, as can be seen from FIG. 2. In the illustrated embodiment, the axis 134 converges with the axis 92 at an angle of 45° as viewed in the sagittal plane. It is contemplated that this angle of convergence as viewed in the sagittal plane could be in the range of from about 30° to about 60°.

The first plate 30 includes a lip portion or lip 150 which is formed as one piece with the main body portion 60 of the first plate. The lip 150, best seen in FIGS. 2 and 5, projects from the second end portion 74 of the main body portion 60 of the first plate 30. The lip 150 projects in the first direction 94 (FIG. 2) when the first plate 30 is mounted on the first vertebra V1.

The lip 150 has a planar configuration as viewed in the first direction 94, for example, as seen in FIG. 2. The lip 150 has an arcuate configuration, as can be seen in FIG. 5, when viewed in a direction parallel to the plane of the outer side surface 62 of the first plate 30. The arcuate configuration of the lip 150 generally follows the arcuate configuration of the inner side surface 64 of the main body portion 60 of the first plate 30. The lip 150 extends continuously between the first and second side portions 68 and 70 of the first plate 30. Alternatively, the lip 150 may be discontinuous at one or more locations along the width of the plate 30.

The lip 150 has an outer end surface 152 (FIG. 2) which is formed as an extension of the second end surface 78 of the main body portion 60 of the first plate 30. An opposite inner end surface 154 (FIGS. 2 and 5) of the lip 150 extends parallel to the outer end surface 152. The lip 150 also has an inner side surface 156 which extends between the inner and outer end surfaces 154 and 152 of the lip 150.

The second and third fastener openings 110 and 130 extend partially through the lip 150. The second fastener opening 110, as can be seen in FIG. 2, extends through the corner between, or intersection of, the lip 150 and the main body portion 60 of the first plate 30. The third fastener opening 130 also extends through the corner between, or intersection of, the lip 150 and the main body portion 60 of the first plate 30.

The second plate 32 (FIG. 7) is generally similar in configuration to the first plate 30 (FIG. 5). The second plate 32 (FIG. 7) is configured, however, so that the head ends of fasteners received in certain fastener openings in the second plate are engageable with the rods 12 and 14 disposed in rod passages in the second plate. This engagement can block movement of the second plate 32 relative to the rods 12 and 14, in a manner described below.

The second plate 32 includes a main body portion 160 which has a planar outer side surface 162 for facing anteriorly or away from the vertebra V2. The main body portion 160 also has an arcuate inner side surface 164 for facing posteriorly or toward the second vertebra V2. The inner side surface 164 of the second plate 32 may engage the anterior surface of the second vertebra V2 when the second plate is connected with the second vertebra as described below.

The main body portion 160 has a central portion 166 which extends laterally between a first side portion 168 and a second side portion 170 of the second plate 32. Because the inner side surface 164 of the second plate 32 has an arcuate configuration, the central portion 166 of the second plate 32 is relatively thin (as viewed in a direction from left to right in FIG. 4) as compared to the first side portion 168 and to the second side portion 170.

The main body portion 160 of the second plate 32 also has first and second end portions 172 and 174. The first end portion 172 of the second plate 32 includes a planar first end surface 176 of the second plate. The second end portion 174 of the second plate 32 includes a planar second end surface 178 of the second plate. The second end surface 178 extends parallel to the first end surface 176.

A first rod passage 180 is formed in the first side portion 168 of the second plate 32. The first rod passage 180 is an opening which extends between the first and second end surfaces 176 and 178 in a direction parallel to the planar outer side surface 162 of the second plate 32. The first rod passage 180 is defined by a cylindrical surface 181 and tapered pilot surfaces 183 and 184 at opposite ends of the cylindrical surface 181. The diameter of the cylindrical surface 181 is slightly greater than the diameter of the first rod 12.

A second rod passage 182 is formed in the second side portion 170 of the second plate 32. The second rod passage 182 is an opening which extends between the first and second end surfaces 176 and 178 in a direction parallel to the planar outer side surface 162 of the second plate 32. The second rod passage 182 extends parallel to and has the same diameter as first rod passage 180. The second rod passage 182 is defined by a cylindrical surface 185 and tapered pilot surfaces 186 and 187 at opposite ends of the cylindrical surface 185. The diameter of the cylindrical surface 185 is slightly greater than the diameter of the second rod 14.

A circular first fastener opening 190 extends through the central portion 166 of the second plate 32. The first fastener opening 190 has an axis 192 (FIGS. 2 and 4) which extends perpendicular to the plane of the outer side surface 162 of the second plate 32. The axis 192 extends in the first direction 94 when the second plate 32 is mounted on the second vertebra V2.

The first fastener opening 190 is partially defined by a larger diameter cylindrical surface 196 (FIG. 8) which extends from the outer side surface 162 of the second plate 32 in a direction into the material of the central portion 166 of the second plate. The cylindrical surface 196 is centered on the axis 192 of the first fastener opening 190. The first fastener opening 190 is partially defined by a smaller diameter cylindrical surface 198 which extends from the inner side surface 164 of the second plate 210 in a direction into the material of the central portion 166 of the second plate, to a location spaced radially inward from the surface 196. The cylindrical surface 198 is centered on the axis 192 of the first fastener opening 190.

An annular shoulder surface 200 (FIGS. 2 and 8) extends radially (relative to the axis 192) between the cylindrical surfaces 196 and 198. The shoulder surface 200 and the larger diameter cylindrical surface 196 define a recess 202 in the outer side surface 162 of the second plate 32.

The main body portion 160 of the second plate 32 also includes a circular second fastener opening 210 formed at a location adjacent to and intersecting the first rod passage 180 in the first side portion 168 of the second plate. The second fastener opening 210 extends through both the second end surface 178 of the second plate 32 and the outer side surface 162 of the second plate.

The second fastener opening 210 is partially defined by a larger diameter cylindrical surface 212 (FIG. 8) which extends from the outer side surface 262 of the second plate 32 in a direction into the material of the first side portion 168 of the second plate. The cylindrical surface 212 is centered on an axis 214 (FIGS. 2 and 4) of the second fastener opening 210. The cylindrical surface 212 intersects the cylindrical surface 181 which defines the first rod passage 180. Thus, the second fastener opening 210 overlaps a portion of the first rod passage 180.

The second fastener opening 210 is partially defined by a smaller diameter cylindrical surface 216 which extends from the inner side surface 264 of the second plate 32 in a direction into the material of the first side portion 168 of the second plate, to a location spaced radially inward from the surface 212. The cylindrical surface 216 is centered on the axis 214 of the second fastener opening 210.

An annular shoulder surface 218 (FIGS. 4 and 8) extends radially (relative to the axis 214) between the cylindrical surfaces 212 and 216. The shoulder surface 218 and the larger diameter cylindrical surface 212 define a recess 220 in the outer side surface 262 of the second plate 32.

The axis 214 of the second fastener opening 210 extends transverse to the axis 192 of the first fastener opening 190. Specifically, the axis 214 of the second fastener opening 210 converges with the axis 192 of the first fastener opening 190 as viewed in a transverse plane at right angles to the vertical axis A, as can be seen from FIG. 4. In the illustrated embodiment, the axis 214 converges with the axis 192 at angle of about 100 as viewed in this transverse plane.

The axis 214 of the second fastener opening 210 also converges with the axis 192 of the first fastener opening 190 as viewed in the sagittal plane, as can be seen in FIG. 2. In the illustrated embodiment, the axis 214 converges with the axis 192 at an angle of 45° as viewed in the sagittal plane. It is contemplated that this angle of convergence could be in the range of from about 30° to about 60° as viewed in the sagittal plane.

The main body portion 160 of the second plate 32 also includes a circular third fastener opening 230 formed at a location adjacent to and intersecting the second rod passage 182 in the second side portion 170 of the second plate. The third fastener opening 230 extends through both the second end surface 178 of the second plate 32 and the outer side surface 162 of the second plate. The distance between the third fastener opening 230 in the second plate 32 and the second fastener opening 210 in the second plate is slightly less than the distance between the third fastener opening 130 in the first plate 30 and the second fastener opening 110 in the first plate.

The third fastener opening 230 is partially defined by a larger diameter cylindrical surface 232 (FIG. 8) which extends from the outer side surface 262 of the second plate 32 in a direction into the material of the second side portion 170 of the second plate. The cylindrical surface 232 is centered on an axis 234 (FIG. 4) of the third fastener opening 230. The cylindrical surface 232 intersects the cylindrical surface 185 which defines the second rod passage 182. Thus, the third fastener opening 230 overlaps a portion of the second rod passage 182.

The third fastener opening 230 is partially defined by a smaller diameter cylindrical surface 236 (FIG. 8) which extends from the inner side surface 264 of the second plate 32 into the material of the second side portion 170 of the second plate to a location spaced radially inward from the surface 232. The cylindrical surface 236 is centered on the axis 234 of the third fastener opening 230.

An annular shoulder surface 238 (FIGS. 4 and 8) extends radially (relative to the axis 234) between the cylindrical surfaces 232 and 236. The shoulder surface 238 and the larger diameter cylindrical surface 232 define a recess 240 in the outer side surface 162 of the second plate 32.

The axis 234 of the third fastener opening 230 is coplanar with the axis 214 of the second fastener opening 210. The axis 234 of the third fastener opening 230 extends transverse to the axis 192 of the first fastener opening 190. Specifically, the axis 234 of the third fastener opening 230 converges with the axis 192 of the first fastener opening 190 as viewed in a transverse plane at right angles to the vertical axis A, as can be seen from FIG. 4. In the illustrated embodiment, the axis 234 converges with the axis 192 at an angle of about 10° as viewed in this transverse plane.

The axis 234 of the third fastener opening 230 also converges with the axis 192 of the first fastener opening 190 as viewed in the sagittal plane, as can be seen from FIG. 2. In the illustrated embodiment, the axis 234 converges with the axis 192 at an angle of 45°. It is contemplated that this angle of convergence as viewed in the sagittal plane could be in the range of from about 30° to about 60°.

The second plate 32 includes a lip portion or lip 250 which is formed as one piece with the main body portion 160 of the second plate. The lip 250, best seen in FIGS. 4 and 7, projects from the second end portion 174 of the main body portion 160 of the second plate 32. The lip 250 projects in the first direction 94 (FIG. 2) when the second plate 32 is mounted on the second vertebra V2.

The lip 250 has a planar configuration as viewed in the first direction 94, for example, as seen in FIG. 2. The lip 250, as viewed in a direction parallel to the plane of the outer side surface 162 of the second plate 32, has an arcuate configuration generally following the arcuate configuration of the inner side surface 164 of the main body portion 160 of the second plate 32. The lip 250 extends continuously between the first and second side portions 168 and 170 of the second plate 32. Alternatively, the lip 250 may be discontinuous at one or more locations along the width of the second plate 32.

The lip 250 has an outer end surface 252 (FIG. 2) which is formed as an extension of the second end surface 178 of the main body portion 160 of the second plate 32. An opposite inner end surface 254 (FIGS. 2 and 8) of the lip 250 extends parallel to the outer side surface 252. The lip 250 also has an inner side surface 256 which extends between the inner and outer end surfaces 252 and 254 of the lip 250. The second and third fastener openings 210 and 230 extend partially through the lip 250. The second fastener opening 210, as well as the third fastener opening 230, extend through the corner between, or intersection of, the lip 250 and the main body portion 160 of the second plate 32.

The fasteners 38, 40, 42, 44, 46, and 48, which connect the first plate 30 with the first vertebra V1 and the second plate 32 with the second vertebra V2, are identical to each other. Because the fasteners 38–48 are identical, only the fastener 40 is described herein in detail.

The fastener 40 (FIG. 3) includes a sleeve 300 and an expander 310. The sleeve 300 has a hollow, elongate shank portion 302 centered on a longitudinal central axis 304 of the fastener 40. The shank portion 302 defines a cylindrical central opening 308 in the sleeve 300. A coarse external helical thread convolution 306 is formed on the outer peripheral surface of the shank portion 302 of the sleeve 300.

The shank portion 302 of the sleeve 300 is radially and axially slotted so that the shank portion is expandable radially. A series of projections (not shown) are formed on the inner surface of the sleeve 300 for engagement by the expander 310 to expand the shank portion 302 of the sleeve in a manner described below.

A head end portion 314 of the sleeve 300 has a cylindrical outer side surface 316. An annular lip or rim 318 extends around the head end portion 314 of the sleeve 300 and projects radially outward from the outer side surface 316. The head end portion 314 of the sleeve 300 has a conical inner side surface 320 and a conical inner side surface 322. The conical inner side surface 322 merges with an internal thread convolution 324 formed on the sleeve 300.

The head end portion 314 of the sleeve 300 is radially and axially slotted to define four segments 326 of the head end portion. The four segments 326 are movable radially relative to each other and to the axis 304 of the fastener 40 so that the head end portion 314 of the sleeve 300 is expandable radially.

The expander 310 has a head end portion 340 and a shank portion 342. An inner end 344 of the shank portion 342 of the expander 310 is slightly larger in diameter than the cylindrical central opening 308 in the sleeve 300.

The head end portion 340 of the expander 310 has an X-shaped driver slot 346 for receiving a driving tool for rotating the expander relative to the sleeve 300. The head end portion 340 has a conical outer side surface 348 and a conical outer side surface 350. The conical outer side surface 350 on the head end portion 340 of the expander 310 has a different angle of taper than does the conical inner side surface 322 on the head end portion 314 of the sleeve 300.

The conical outer side surface 350 on the head end portion 340 of the expander 310 merges with an external thread convolution 352 formed on the expander 310. The external thread convolution 352 on the expander 310 screws into the internal thread convolution 324 on the sleeve 300.

To install the apparatus 10 on the spinal column C, the rods 12 and 14 are first assembled with the plates 30 and 32. Specifically, the first rod 12 is inserted through the first rod passage 80 in the first plate 30 and through the first rod passage 180 in the second plate 32. One of the tapered pilot surfaces 83 and 84 on the first plate 30, and one of the tapered pilot surfaces 183 and 184 on the second plate 32, guide insertion of the first rod 12. The second rod 14 is inserted through the second rod passage 82 in the first plate 30 and through the second rod passage 182 in the second plate 32. One of the tapered pilot surfaces 86 and 87 on the first plate 30, and one of the tapered pilot surfaces 186 and 187 on the second plate 32, guide insertion of the second rod 14.

The assembly of the rods 12 and 14 and the plates 30 and 32 is then positioned over the exposed anterior surface of the spinal column C. The first plate 30 (FIG. 2) is positioned adjacent to the first vertebra V1 so that the first end surface 154 on the lip 150 of the first plate engages a lower surface 360 on the first vertebra V1. The lower surface 360 on the first vertebra V1 faces toward the second vertebra V2. The second plate 32 is positioned adjacent to the second vertebra V2 so that the first end surface 254 on the lip 250 of the second plate engages an upper surface 362 on the second vertebra V2. The upper surface 362 on the second vertebra V2 faces toward the first vertebra V1.

With the first plate 30 on the first vertebra V1, and the second plate 32 on the second vertebra V2, a suitable drill guide and drill (not shown) are used to drill fastener openings in the first vertebra V1 and in the second vertebra V2.

The fasteners 38, 40 and 42 are inserted to connect the first plate 30 with the first vertebra. The insertion and securing of the fastener 40, although not necessarily performed first, will be described as exemplary.

The sleeve 300 of the fastener 40 is inserted through the second fastener opening 110 in the first plate 30. The sleeve 300 of the fastener 40 is threaded into the drilled opening in the vertebra V1 in a known manner (not shown) to fix the sleeve in position in the vertebra V1. The unexpanded head portion 314 of the sleeve 300 is disposed in the recess 120 in the first plate 30.

The expander 310 of the fastener 40 is then inserted into the sleeve 300. The externally threaded portion 352 of the expander 310 is screwed into the internal threads 324 on the sleeve 300. When the expander 310 is fully screwed into the sleeve 300, the inner end portion 344 of the expander 310 causes the shank portion 302 of the sleeve to expand radially outward, helping to lock the sleeve in place in the vertebra V1. When the expander 310 is fully screwed into the sleeve 300, the head portion 340 of the expander 310 engages the head portion 314 of the sleeve 300. The head portion 340 of the expander 310 wedges the locking segments 326 on the sleeve 300 radially outward into engagement with the first plate 30 to rigidly lock the fastener 40 in position relative to the first plate. The head of the fastener 40 is adjacent to the lip 150.

The remaining fasteners 38 and 42 for the first plate 30 are similarly secured to the vertebra V1 and are rigidly locked to the first plate. The heads of the fasteners 38 and 42 are adjacent to the lip 150. As a result, the first plate 30 is securely connected with the first vertebra V1.

The fasteners 44, 46 and 48 are similarly used to connect the second vertebra V2 and the second plate 32. The heads of the fasteners 44, 46, and 48 are adjacent to the lip 250. As a result, the fasteners 44, 46 and 48 are rigidly locked to the plate 32 and the plate 32 is securely connected with the second vertebra V2.

As can be seen in FIG. 2, the fastener 40 (as well as the fastener 42, not shown in FIG. 2) extends at an angle (upward as viewed in FIG. 2) to the lip 150. Accordingly, when the fasteners 40 and 42 are tightened into the first vertebra V1, the fasteners tend to draw the lip 150 of the first plate 30 tightly against the surface 360 of the vertebra, that is, in an upward direction as viewed in FIG. 2. At the same time, the fasteners 40 and 42, as well as the fastener 38, tend to draw the main body portion 60 of the first plate 30 tightly against the anterior surface of the first vertebra V1, that is, in a direction to the left as viewed in FIG. 2. Accordingly, it can be seen that tightening the fasteners 38, 40 and 42 tends to draw the first plate 30 in two directions against the first vertebra V1.

The first fastener 38 has a longitudinal central axis which is coincident with the axis 92 of the first fastener opening 90 when the first fastener 38 is disposed in the first fastener opening 90 in the first plate 30. When the second fastener 40 is disposed in the second fastener opening 110 in the first plate 30, the longitudinal central axis 304 of the second fastener 40 is coincident with the axis 114 of the second fastener opening 110.

As described above, the axis 92 of the first fastener opening 90 and the axis 114 of the second fastener opening 110 converge at an acute angle as viewed in the sagittal plane (FIG. 2). Therefore, the longitudinal axis of the first fastener 38 and the longitudinal axis 304 of the second fastener 40 converge at an acute angle as viewed in the sagittal plane (FIG. 2) when the first and second fasteners 38 and 40 connect the first plate 30 with the first vertebra V1. In the illustrated embodiment, the axis of the first fastener 38 and the axis 304 of the second fastener 40 converge at an angle of about 45° as viewed in the sagittal plane. It is contemplated that this angle of convergence in the sagittal plane could be in the range of from about 30° to about 60°.

When the third fastener 42 is disposed in the third fastener opening 130 in the first plate 30, the longitudinal central axis of the third fastener 42 is coincident with the axis 134 of the third fastener opening 130. As described above, the axis 92 of the first fastener opening 90 and the axis 134 of the third fastener opening 110 converge at an acute angle as viewed in the sagittal plane (FIG. 2). Therefore, the longitudinal axis of the first fastener 38 and the longitudinal axis of the third fastener 42 converge at an acute angle as viewed in the sagittal plane (FIG. 2) when the first and third fasteners 38 and 42 connect the first plate 30 with the first vertebra V1. In the illustrated embodiment, the axis of the first fastener 38 and the axis of the third fastener 42 converge at an angle of about 45° as viewed in the sagittal plane. It is contemplated that this angle of convergence in the sagittal plane could be in the range of from about 30° to about 60°.

The second plate 32 is, in a similar manner, secured in position relative to the second vertebra V2. Tightening the fasteners 44, 46 and 48 tends to draw the second plate 32 in two directions against the second vertebra V2.

When the first fastener 44, the second fastener 46, and the third fastener 48 connect the second plate 32 with the second vertebra V2, the axis of the first fastener 44 and the axis of the second fastener 46 converge at an acute angle as viewed in the sagittal plane (FIG. 2). Also, the axis of the first fastener 44 and the axis of the third fastener 48 converge at an acute angle as viewed in the sagittal plane (FIG. 2). In the illustrated embodiment, these axes converge at an angle of about 45° as viewed in the sagittal plane. It is contemplated that this angle of convergence in the sagittal plane could be in the range of from about 30° to about 60°.

The fact that there are three screws which secure each one of the plates 30 and 32 to the spinal column C also helps to maintain proper placement of the plates. These features help the apparatus 10 maintain the vertebrae V1 and V2 in place when the cervical spine is subjected to various degrees of motion of the human head.

When the second plate 32 is being connected with the second vertebra V2, the outer fasteners 46 and 48 secure the second plate and the second vertebra. The fasteners 46 and 48 also serve to interlock the second plate 32 with the rods 12 and 14. This is because the locking segments 326 on the sleeves 300 of the fasteners 46 and 48 (FIG. 4) move radially outward into engagement with the rods 12 and 14, respectively, when each fastener's expander is fully screwed into the fastener's sleeve. The engagement between the fasteners 46 and 48 and the rods 12 and 14 blocks movement of the fasteners 46 and 48 relative to the rods. The radial movement of the locking segments 326 of the fasteners also causes the rods to be clamped against the cylindrical surfaces 181 and 185 which define the rod passages 180 and 182, respectively in the second plate 32. As a result, the expanded fasteners 46 and 48 block movement of the second plate relative to the rods 12 and 14.

The first plate 30, in contrast, is movable relative to the rods 12 and 14, because the second and third fastener openings 110 and 130 are spaced apart from the rod passages 80 and 82. Therefore, the first plate 30 is movable relative to the second plate 32.

Accordingly, the first vertebra V1 is movable vertically downward relative to the second vertebra V2. This relative movement allows for the maintaining of a load on bone graft placed between the vertebrae V1 and V2. If the first plate 30 were not movable vertically downward relative to the second plate 32, then the distance between the vertebrae V1 and V2 would be fixed. If bone graft were placed between the vertebrae V1 and V2 and the bone graft resorbed sufficiently, the bone graft could possibly shrink out of engagement with one or both of the vertebrae V1 and V2. Allowing relative movement of the plates 30 and 32 can help to maintain a desired load on bone graft placed between the vertebrae V1 and V2 and maintains the vertebrae in contact with the bone graft to facilitate bone growth. The lips 150 and 250 on the plates 30 and 32 are, preferably, configured so that the lips do not contact bone graft placed between the vertebrae.

The caps 50 and 54 on the rods 12 and 14, respectively, limit movement of the first vertebra V1 in a direction away from the second vertebra V2. This helps to maintain a load on the bone graft and maintain the vertebrae V1 and V2 in contact with the bone graft.

Figure 9:
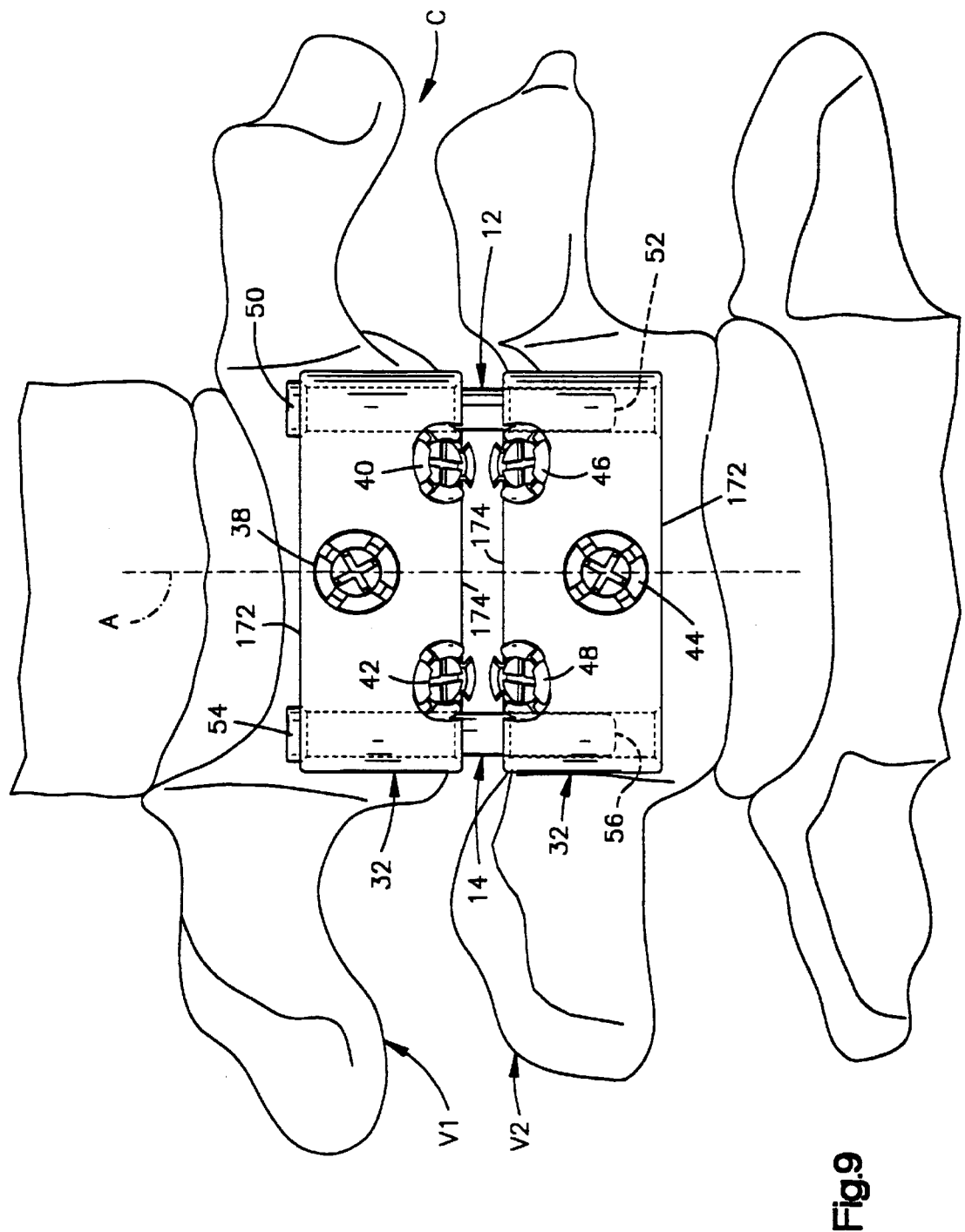
FIG. 9 is a view similar to FIG. 1 of a modified embodiment of the invention.

It may not be necessary or desirable, in some circumstances, to use a dynamic (movable) plate such as the plate 30. In such circumstances, two locking plates identical to the plate 32 can be used in the same apparatus 10. Such a system is illustrated in FIG. 9. The upper plate 32 (FIG. 9) is fixed in position relative to the vertebra V1 and to the rods 12 and 14. The lower plate 32 (FIG. 9) is fixed in position relative to the vertebra V2 and to the rods 12 and 14. Accordingly, the apparatus 10 (FIG. 9) blocks relative movement between the vertebrae V1 and V2.

Figure 10:
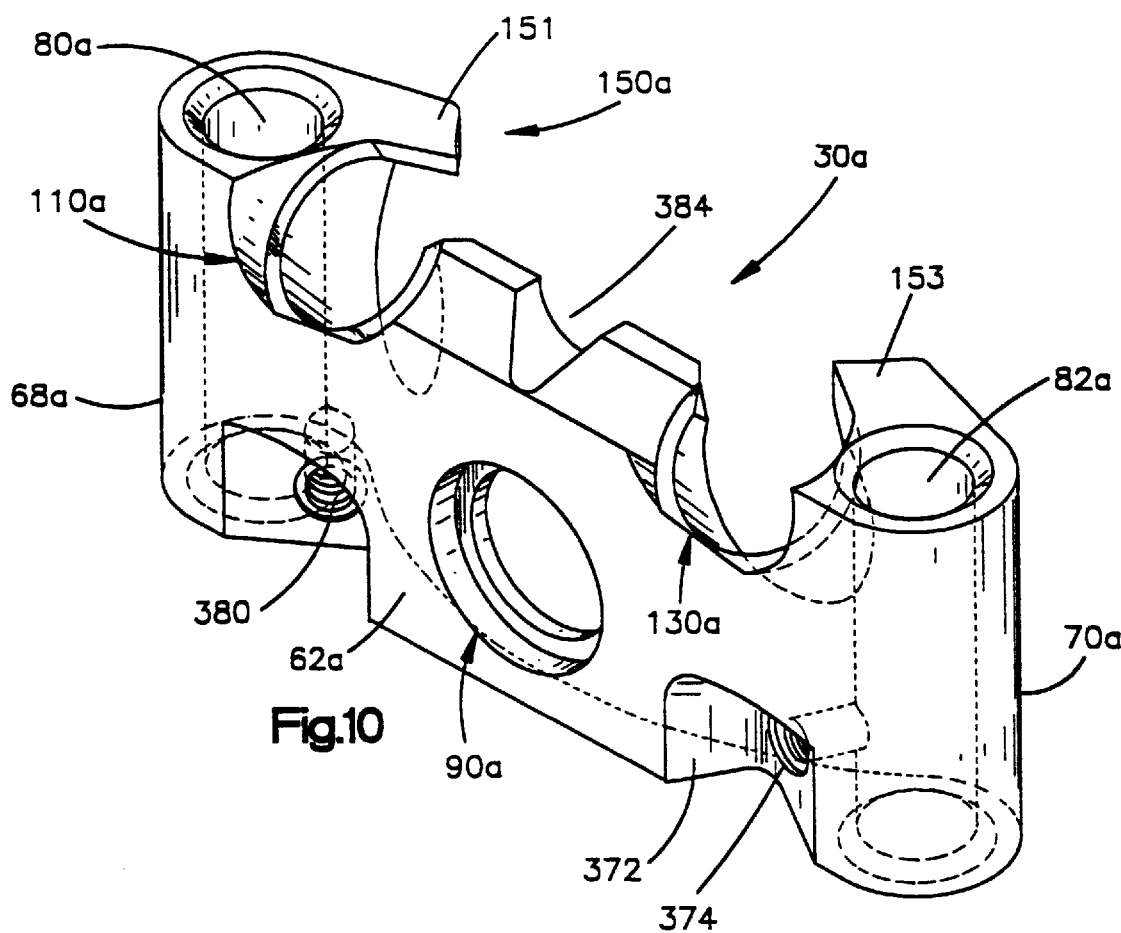
FIG. 10 is a perspective view of a plate which is constructed in accordance with a second embodiment of the present invention.
Figure 11:
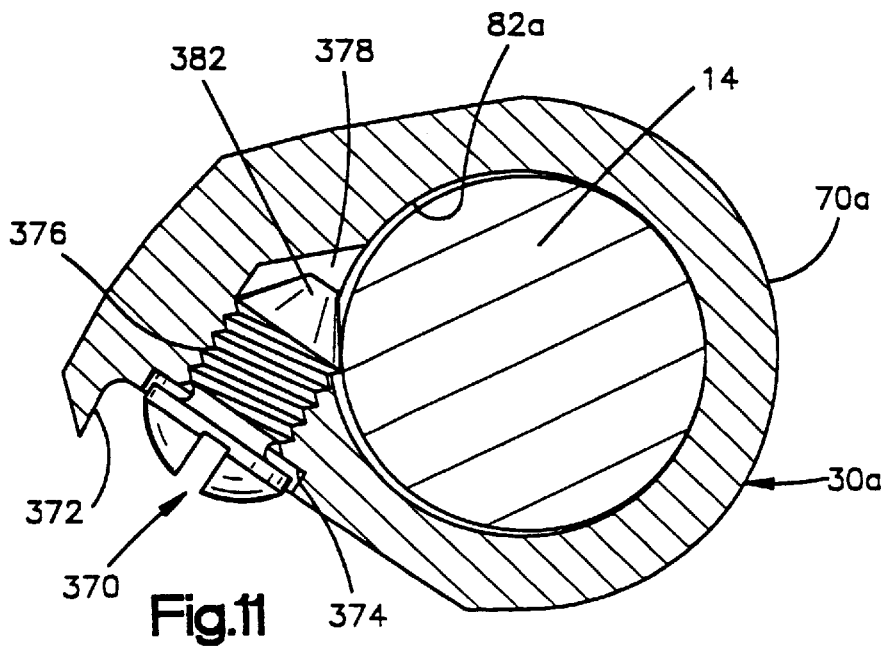
FIG. 11 is an enlarged sectional view of a portion of the plate of FIG. 10 and showing a set screw and rod associated with the plate.

FIGS. 10 and 11 illustrate a plate 30a which is constructed in accordance with a second embodiment of the present invention. The plate 30a can be substituted, in the apparatus 10, for the plate 30. The plate 30a is generally similar to the plate 30 (FIGS. 5 and 6), and similar reference numerals are used to designate similar parts, with the suffix "a" added in FIGS. 10 and 11 for clarity.

In the plate 30a, a pair of set screws 370 are provided for engaging the rods 12 and 14 to block movement of the plate, and thereby its associated bone portion, relative to the rods. Specifically, the outer side surface 62a of the plate 30a is recessed at 372 adjacent to the second rod passage 82a. A seat 374 extends inwardly from the recess 372 to a threaded opening 376. An inner end portion 378 of the opening 376 intersects with the second rod passage 82a. On the opposite side portion 68a of the plate 30a, a second threaded opening 380 intersects the first rod passage 80a.

After the plate 30a is assembled with the rods 12 and 14 and positioned adjacent to the spinal column C, fasteners such as the fasteners 38–42 are inserted through fastener openings 90a, 110a, and 130a in the plate 30a, to secure the plate to its associated bone portion. The head end portions of the fasteners for the plate 30a do not engage the rods 12 and 14, and do not clamp the rods against the plate 30a.

A set screw 370 is threaded into the opening 376. An inner end portion 382 of the set screw 370 engages the cylindrical outer surface of the second rod 14. The engagement of the set screw 370 with the second rod 14 clamps the rod against the second side portion 70a of the plate 30a. Another set screw 370 is threaded into the opening 380 to engage the first rod 12 and clamp the first rod against the first side portion 68a of the plate 30a.

As a result, the set screws 370, the rods 12 and 14, and the plate 30a are interlocked. The plate 30a is movable relative to (along the length of) the rods 12 and 14. Because the plate 30a is fixed to its associated bone portion, then the bone portion also is movable relative to the rods 12 and 14.

In the plate 30a, a portion of the lip 150a is removed at the location of the fastener openings 110a and 130a, to provide better visibility. This provides two lip segments 151 and 153 at the side portions 68a and 70a, respectively, of the plate 30a. The lip segments 151 and 153 are spaced apart on opposite sides of the longitudinal axis, or centerline, of the plate 30a. A portion of the lip 150a also is removed at the lateral center of the plate 30a, and a notch 384 is provided in the plate 30a, again to increase visibility.

From the above description of the invention, those skilled in the art will perceive improvements, changes and modifications in the invention. Such improvements, changes and modifications within the skill of the art are intended to be covered by the appended claims.

Having described the invention, we claim:

1. An apparatus for use in retaining a first vertebra of a spinal column in a desired spatial relationship with a second vertebra of the spinal column with a graft between the vertebra, said apparatus comprising:

a plate adapted to be fastened to the first vertebra, the plate including a body and a lip projecting from the body, the lip being adapted to engage a surface of the first vertebra that faces toward the second vertebra and to remain spaced apart from the graft, a substantially rigid member positionable along the spinal column coupled to the plate.

2. The apparatus of claim 1, wherein:

the plate is formed to include a first end and a second end, and the lip projects from the second end.

3. The apparatus of claim 1, wherein the body includes an outer side surface and the lip extends from the plate generally transverse to the outer side surface.

4. The apparatus of claim 3, wherein the outer side surface is generally planar.

5. The apparatus of claim 1, wherein the body is formed to include first and second openings.

6. The apparatus of claim 5, further comprising a first fastener extendable through the first opening to couple the body to the first vertebra, the first fastener having a first longitudinal axis.

7. The apparatus of claim 6, further comprising a second fastener extendable through the second opening to couple the body to the first vertebra, the second fastener having a second longitudinal axis.

8. The apparatus of claim 1, wherein the plate is adapted to fasten to the second vertebra.

9. An apparatus for use in retaining a first vertebra of a spinal column in a desired spatial relationship with a second vertebra of the spinal column with a graft between the vertebra, said apparatus comprising:

a plate adapted to be fastened to the first vertebra, the plate including a body and a lip projecting from the body, the lip being adapted to engage a surface of the first vertebra that faces toward the second vertebra and to remain spaced apart from the graft, wherein the body includes first and second sides and the lip has a first segment adjacent to the first side and a second segment adjacent to the second side.

10. The apparatus of claim 9, wherein the lip extends substantially continuously along the body between the first and second sides.

11. An apparatus for use in retaining a first vertebra of the spinal column in a desired spatial relationship with the second vertebra of the spinal column with a graft between the vertebra, said apparatus comprising:

a plate adapted to be fastened with the vertebra, the plate including a body and a lip projecting from the body, the lip being adapted to engage a surface of the first vertebra, face toward the second vertebra, and extend around the graft;

the body being formed to include first and second openings;

a first fastener extendable through the first opening to couple the body with the first vertebra, the first fastener having a first longitudinal axis; and a second fastener extendable through the second opening to couple the body to the first vertebra, the second fastener having a second longitudinal axis;

the first longitudinal axis and the second longitudinal axis converging at an acute angle.

12. An apparatus for use in retaining a first vertebra of a spinal column in a desired spatial relationship with a second vertebra of the spinal column with a graft between the vertebra, said apparatus comprising:

a substantially rigid member positionable along the spinal column, and a plate coupled to the substantially rigid member and adapted to be fastened with the first vertebra, the plate being formed to include a body and a lip projecting from the body and being adapted to engage a surface of the first vertebra.

13. The apparatus of claim 12, wherein the body includes a corner defined by a first outer surface and a second outer surface extending from the first outer surface, the body further including first and second openings extending through the corner.

14. The apparatus of claim 12, wherein the body has first and second sides and the lip has a first segment adjacent to the first side.

15. The apparatus of claim 12, wherein the body includes a first end aid a second end disposed intermediate the first end and the second vertebra the body further including first and second openings disposed in the second end.

16. The apparatus of claim 12, wherein a corner defined by a first outer surface and a second outer surface extending from the first outer surface, the body further including first and second openings through the corner.

17. The apparatus of claim 16, further comprising a first fastener formed for extension through the first opening into the first vertebra and a second fastener formed for extension through the second opening into the second vertebra.

18. An apparatus for use in retaining a first vertebra of a spinal column in a desired spatial relationship with the second vertebra of the spinal column with a graft between the vertebra, said apparatus comprising:

a longitudinal member positionable along the spinal column;

a plate coupled to the longitudinal member and adapted to be fastened with the first vertebra, the plate being formed to include a body and a lip projecting from the body and being adapted to engage a surface of the first vertebra;

the body including first and second sides and the lip including a first segment adjacent to the first side;

the lip including a second segment adjacent to the second side.

19. The apparatus of claim 18, wherein the lip extends substantially continuously along an edge between the first and second sides.

20. An apparatus for use in retaining a first vertebra of a spinal column in a desired spatial relationship with a second vertebra of the spinal column with a graft between the vertebra, said apparatus comprising:

a plate adapted to be fastened to the first vertebra, the plate including a body formed to include an opening therethrough and a lip projecting from the body, the lip being adapted to engage a surface of the first vertebra, a fastener formed for extension through the opening into the first vertebra; and a substantially rigid member positionable along the spinal column coupled to the plate.

21. The apparatus of claim 20, wherein the body has first and second ends and the opening is formed adjacent to the second end.

22. The apparatus of claim 21, wherein the lip projects from the second end of the body.

23. An apparatus for use in retaining a first vertebra of a spinal column in a desired spatial relationship with a second vertebra of the spinal column with a graft between the vertebra, said apparatus comprising:

a plate adapted to be fastened with the first vertebra, the plate including a body formed to include an opening therethrough and a lip projecting from the body, the lip being adapted to engage a surface of the first vertebra; and a fastener formed for extension through the opening into the first vertebra;

the body having first and second ends and the opening being formed adjacent to the second end;

the lip projecting from the second end of the body;

the body including first and second sides and the lip extending between the first and second sides.

* * * * *

UNITED STATES PATENT AND TRADEMARK OFFICE
CERTIFICATE OF CORRECTION

PATENT NO. : 6,214,005 B1  Page 1 of 1
DATED : April 10, 2001
INVENTOR(S) : Edward C. Benzel, Hansen A. Yuan, Alex Dinello, Michael H. Wefers, Aaron C. Smith It is certified that error appears in the above-identified patent and that said Letters Patent is hereby corrected as shown below:

Column 14, claim 10,
Line 8, please delete "body" and insert -- edge --

Column 14, claim 15,
Line 49, please delete "aid" and insert -- and --

Signed and Sealed this

Thirteenth Day of November, 2001

Attest:

*Nicholas P. Godici*

NICHOLAS P. GODICI
*Attesting Officer*   *Acting Director of the United States Patent and Trademark Office*